United States Patent [19]

Olmedo

[11] Patent Number: 5,050,592

[45] Date of Patent: Sep. 24, 1991

[54] PENILE PROSTHESIS

[76] Inventor: Raul Olmedo, 42 Clemenceau, Cordoba 5000, Argentina

[21] Appl. No.: 519,657

[22] Filed: May 7, 1990

[51] Int. Cl.⁵ .............................................. A61F 2/26
[52] U.S. Cl. ...................................................... 128/79
[58] Field of Search ............................................ 128/79

[56] References Cited

U.S. PATENT DOCUMENTS

| 4,483,331 | 11/1984 | Trick | 128/79 |
| 4,619,251 | 10/1986 | Helms et al. | 128/79 |
| 4,666,428 | 5/1987 | Mattioli et al. | 128/79 |

Primary Examiner—Cary E. O'Connor
Attorney, Agent, or Firm—A. W. Fisher, III

[57] ABSTRACT

A penile prosthesis movable between a flaccid and erect position comprising an elongated member including a flexible substantially cylindrical proximal section and elongated malleable substantially cylindrical distal section having an intermediate truncated conical section formed therebetween, the elongated malleable substantially cylindrical distal section includes a centrally disposed inner memory member extending longitudinally therethrough to selectively maintain the penile prosthesis in the flaccid or erect position.

6 Claims, 2 Drawing Sheets

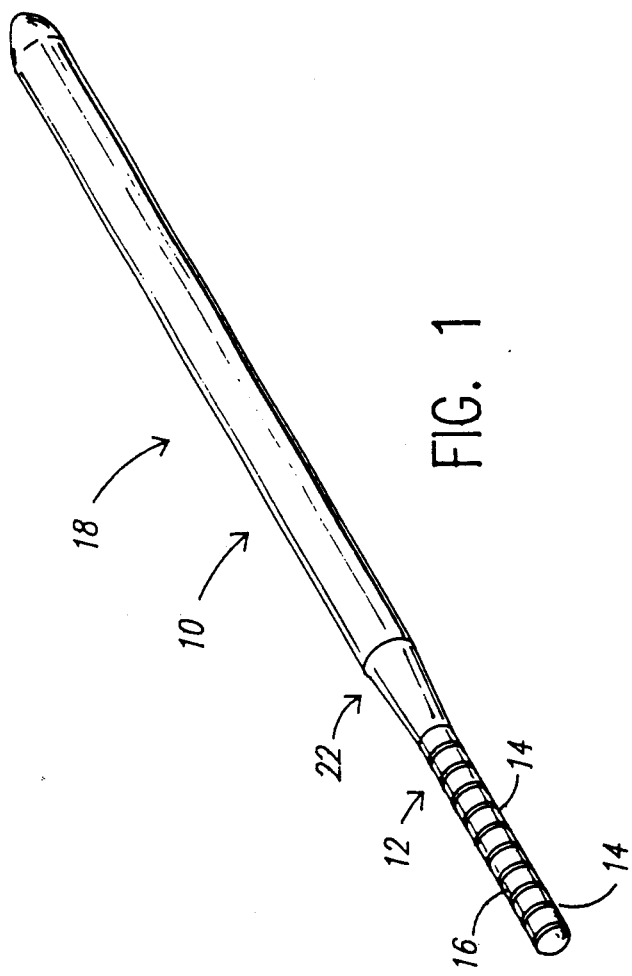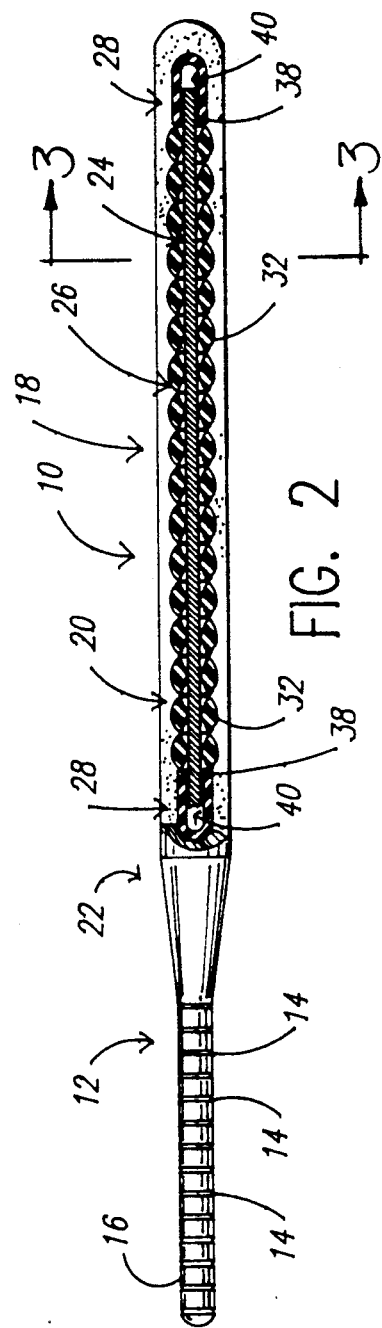

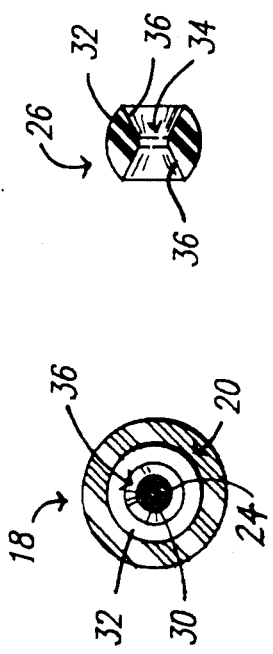
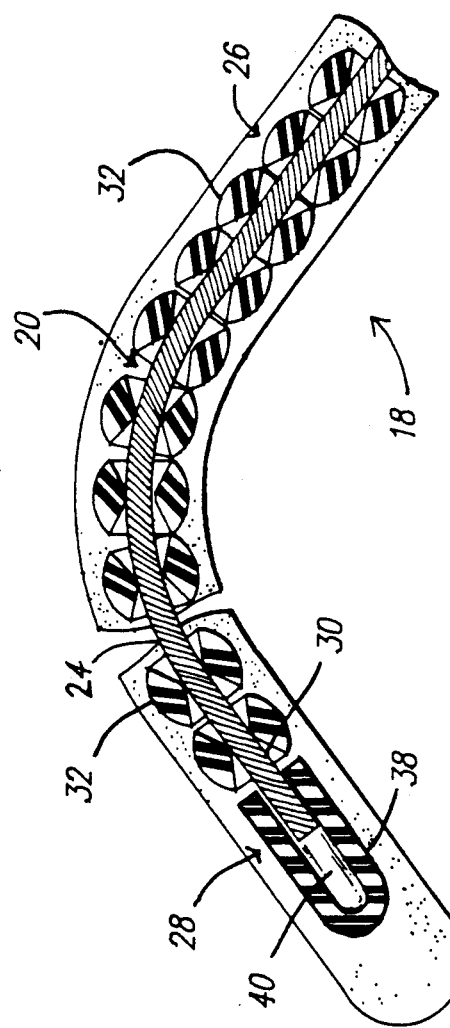

PENILE PROSTHESIS

BACKGROUND OF THE INVENTION

1. Field of The Invention

A penile prosthesis movable between a flaccid and erect position including a flexible proximal section and a malleable distal section.

2. Description of The Prior Art

Numerous devices have been developed to be implanted in a flaccid penis capable of simulating an erection.

U.S. Pat. No. 4,545,081 teaches a penile prosthesis including a minor length member and major length member enabling insertion into the crus and the corpus cavernosum respectively. A quick engageable connector is formed on adjacent ends of each member for joining the members together as a unit after each member is properly positioned in the patient. Penile posture control is accomplished by an axially extending multiple jointed spine within a silicone rubber casing. The spine is formed with alternate tubular and spherical links retained in an articulating assembly by an axial wire. Each spherical link is formed with a pair of diametric extensions projecting into the bores of adjacent tubular links and a diametric bore through the extensions through which the wire passes. The extensions serve to limit the articulation between adjacent links.

U.S. Pat. No. 3,987,789 discloses a prosthesis for simulating an erection including a malleable rod disposed within a generally tubular, physiologically inert plastic body.

U.S. Pat. No. 4,522,198 shows a penile prosthesis implanted in the penis for the treatment of impotence comprising an articulated column having alternating joints with a switch aligned for reversibly extending the articulated column against the ends of the sheath and tensioning a tension member whereby frictional resistance at the joints increases to simulate an erection.

U.S. Pat. No. 4,392,562 teaches a prosthesis including an elongated malleable element to enable the prosthesis to be conformed to a variety of shapes. A bend-limiting member is positioned next to the elongated malleable element to limit the radius of bend thereof to minimize damage or weakening to the malleable element through extreme bending.

U.S. Pat. No. 4,066,073 discloses a penile implant comprising an elongated rod of silicone rubber or other suitable material positionable within the corpus cavernosum of the penis. The elongated rod includes axially arrayed sections. A proximal section is positioned adjacent the pubis; while a longer distal section is disposed in the pendulus penis. The distal and proximal sections are separated by a very flexible hinge section.

Additional example of the prior art are found in: U.S. Pat. No. 1,462,000; U.S. Pat. No. 3,446,206; U.S. Pat. No. 3,773,040; U.S. Pat. No. 3,832,996; U.S. Pat. No. 3,853,122; U.S. Pat. No. 3,893,456; U.S. Pat. No. 4,151,840; U.S. Pat. No. 4,151,841; U.S. Pat. No. 4,177,805; U.S. Pat. No. 4,411,260; U.S. Pat. No. 4,449,520; U.S. Pat. No. 4,566,446; U.S. Pat. No. 4,589,405; U.S. Pat. No. 4,594,998; U.S. Pat. No. 4,625,716 and German 2740263.

SUMMARY OF THE INVENTION

The present invention relates to a penile prosthesis movable between a flaccid and erect postiion comprising an elongated member constructed of physiologically inert medical grade synthetic material. The elongated member comprises a flexible proximal section and an elongated malleable distal section having a centrally disposed inner memory member extending longitudinally therethrough. The centrally disposed inner memory member comprises an elongated flexible element extending through a plurality of stiffening elements. Opposite ends of the elongated flexible element are coupled to a pair of anchor members. Each stiffening element comprises a substantially spherical member having a centrally disposed channel formed therethrough to receive the elongated flexible element.

After an appropriate incision, the corpus cavernosum is dilated to receive the penile prosthesis. The appropriate anatiomical measurements are made to insure that the flexible proximal section is positioned at the base of the penis below the pelvic bone. Once the penile prosthesis is in place, the incision is closed.

In use, the penile prosthesis is simply bent in any area along the length thereof the establish the flaccid or erect position.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 1 is a perspective view of the penile prosthesis.

FIG. 2 is a cross-sectional side view of the penile prosthesis.

FIG. 3 is an end view of the elongated malleable substantially cylindrical distal section taken along being 3—3 of FIG. 2.

FIG. 4 is a cross-sectional side view of the stiffening element.

FIG. 5 is a detailed partial cross-sectional side view of the elongated malleable substantially cylindrical distal section.

Similar reference characters refer to similar parts throughout the several views of the drawings.

DETAILED DESCRIPTION OF THE PREFERRED EMBODIMENT

As shown in FIGS. 1 and 2, the present invention relates to a penile prosthesis movable between a flaccid and erect position. More specifically, the penile prosthesis comprises an elongated member generally indicated as 10 constructed of physiolgically inert medical grade synthetic material such as silicone.

As shown in FIGS. 1 and 2, the elongated member 10 comprises a flexible substantially cylindrical proximal section generally indicated as 12 having a plurality of axially spaced sizing grooves each indicated as 14 formed in the outer surface 16 thereof and an elongated malleable substantially cylindrical distal section generally indicated as 18 having a centrally disposed inner memory member generally indicated as 20 extending longitudinally therethrough. The elongated member 10 further includes an intermediate truncated conical section generally indicated as 22 formed between the flexible substantially cylindrical proximal section 12 and the elongated malleable substantially cylindrical distal section 18.

As shown in FIGS. 2, 3 and 5, the centrally disposed inner memory member 20 comprises an elongated flexible element generally indicated as 24 extending through a plurality of hard stiffening elements each generally indicated as 26. Opposite ends of the elongated flexible element 24 are operatively coupled to a pair of anchor members each generally indicated as 28 as described more fully hereinafter. The elongated flexible element 24 comprises a plurality of metallic filaments each indicated as 30 in twisted, woven disposition relative to each other. Each hard stiffening element 26 comprises a substantially spherical member 32 of Teflon or similar hard material having a centrally disposed channel 34 formed therethrough to receive the elongated flexible element 24. Opposite ends of each centrally disposed channel 34 terminate in a substantially conical opening 36 to preclude or eliminate damage of the elongated flexible element 24 when bent. The plurality of hard stiffening element 28 create more rigidity during the erection state because the Teflon is harder than silicone.

As best shown in FIGS. 2 and 5, each anchor member 28 comprises a substantially cylindrical body 38 having a centrally disposed channel 40 formed therein to slidingly receive the corresponding end of the elongated flexible member 24. As the penile prosthesis is bent the ends of the elongated flexible element 24 moves within the centrally disposed channels 40 as adjacent hard stiffening elements 26 engage each other. The flexible substantially cylindrical proximal section 12 may be trimmed to vary the length of the penile prosthesis by cutting the appropriate axially spaced sizing groove 14. After appropriate incision, the corpus cavernosum is dilated distally and proximally to accept the penile prosthesis.

In use, the penile prosthesis is simply bent in any area along the length thereof to establish the flaccid or erect position.

It will thus be seen that the objects set forth above, among those made apparent from the preceding description are efficiently attained and since certain changes may be made in the above construction without departing from the scope of the invention, it is intended that all matter contained in the above description or shown in the accompanyiny drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A penile prosthesis movable between a dependent and erect position comprising an elongated member including a flexible substantially cylindrical proximal section and an elongated malleable substantially cylindrical distal section, said elongated malleable substantially cylindrical distal section includes a centrally disposed inner memory member comprising an elongated flexible element extending through a plurality of stiffening elements extending longitudinally through said elongated malleable cylindrical distal section to selectively maintain the penile prosthesis in the dependent or erect position, each said stiffening elements comprises an outer arcuate surface having a substantially flat surface formed on each end thereof, each said substantially flat surface includes a corresponding conical recess formed therein, said corresponding conical recesses of each said stiffening element being connected by a centrally disposed channel including a side wall to receive said elongated flexible element therethrough such that said side walls engage said elongated flexible element to control the position of said flexible substantially cylindrical proximal section and to prevent contact of said elongated flexible element with said substantially flat surfaces.

2. The penile prosthesis of claim 1 wherein said elongated flexible element comprises a plurality of filaments.

3. The penile prosthesis of claim 1 wherein said flexible proximal section include at least one sizing groove formed in the outer surface thereof.

4. The penile prosthesis of claim 3 wherein said flexible proximal section further includes as plurality of axially spaced sizing grooves.

5. The penile prosthesis of claim 1 further including an intermediated section formed between said flexible proximal section and said elongated malleable distal section.

6. The penile prosthesis of claim 1 further including an anchor member disposed at opposite ends of said elongated malleable substantially cylindrical distal section disposed to slidingly receive opposite ends of said elongated flexible element, each said anchor member comprising a body having a centrally disposed channel formed therein to receive said opposite ends of said elongated flexible element therein in mechanically free relationship therewith.

* * * * *